United States Patent [19]

Heiliger et al.

[11] Patent Number: 5,298,583

[45] Date of Patent: Mar. 29, 1994

[54] POLYMER DYESTUFFS AND PREPARATION AND USE THEREOF

[75] Inventors: Ludger Heiliger, Leverkusen; Hans-Ulrich Siegmund, Krefeld; Herbert Hugl, Bergisch Gladbach; Antonius Löbberding, Wuppertal; Eberhard Kuckert, Leverkusen; Bruno Bömer, Bergisch-Gladbach; Thomas Böcker, Düsseldorf; Günther Franke, Leichlingen, all of Fed. Rep. of Germany

[73] Assignee: Bayer Aktiengesellschaft, Leverkusen, Fed. Rep. of Germany

[21] Appl. No.: 875,167

[22] Filed: Apr. 28, 1992

[30] Foreign Application Priority Data

May 3, 1991 [DE] Fed. Rep. of Germany ....... 4114482

[51] Int. Cl.$^5$ ............ C08F 228/02; C08F 220/56; C08F 220/10; C08F 220/06
[52] U.S. Cl. .................... 526/286; 526/305; 526/326; 526/317.1; 526/318.4; 526/307.3; 526/307.7; 526/347; 526/292.7; 526/320; 526/310; 526/273
[58] Field of Search ............ 526/286, 305, 326, 317.1, 526/318.4, 307.3, 307.7, 347, 292.7, 320, 310, 273

[56] References Cited

U.S. PATENT DOCUMENTS 5,030,697  7/1991  Hugl et al. .................. 525/326.9

FOREIGN PATENT DOCUMENTS 0244929  2/1987  European Pat. Off. .
0342052  5/1989  European Pat. Off. .
0361229  9/1989  European Pat. Off. .
2295426  7/1974  France .

Primary Examiner—Joseph L. Schofer
Assistant Examiner—Wu C. Cheng
Attorney, Agent, or Firm—Sprung Horn Kramer & Woods

[57] ABSTRACT

The present invention relates to polymer dyestuffs, i.e. polymer-bound dyestuffs, to a process for their preparation and to their use, for example as markers in analytical procedures. Polymer dyestuffs contain linkable functional groups and are water-soluble under customary conditions of analysis. The polymer portion is usually responsible for this water solubility. The dyestuffs per se are often water-insoluble.

6 Claims, No Drawings

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 30 Nucleotides
( B ) TYPE: Nucleic Acid (C) STRANDEDNESS: Single
(D) TOPOLOGY: Linear (xi) SEQUENCE DESCRIPTION: SEQ ID NO:1:

CTCGGATCCC ATCTTCTCCC CTGAGTCTGT  30

(2) INFORMATION FOR SEQ ID NO: 2:

(i) SEQUENCE CHARACTERISTICS:
(A) LENGTH: 42 Nucleotides
(B) TYPE: Nucleic Acid
(C) STRANDEDNESS: Single
(D) TOPOLOGY: Linear (xi) SEQUENCE DESCRIPTION: SEQ ID NO:2:

ATCTACTGGC TCTTTTTTTT TTTTTTTTT TTTTTTTTTT TT  42

POLYMER DYESTUFFS AND PREPARATION AND USE THEREOF

The present invention relates to polymer dyestuffs, i.e. polymer-bound dyestuffs, to a process for their preparation and to their use, for example as markers in analytical procedures. Polymer dyestuffs contain linkable functional groups and are water-soluble under customary conditions of analysis. The polymer portion is usually responsible for this water solubility. The dyestuffs per se are often water-insoluble.

Known markers which are usable in biological test systems often have the disadvantage of poor workplace safety and of restricted handling only at specially equipped laboratories (radioactivity) or of insufficient stability, for example in enzyme labelling.

Fluorescent polymers and their preparation by means of dyestuffs preferably containing amino groups are known. U.S. Pat. No. 4,166,105 describes reagents which are suitable for the detection of specific reactants, for example antigens, and consist of an antibody-bound polymer which contains a large number of dyestuff molecules.

The dyestuff polymers have terminal functional groups, which can be utilised for linkage with the protein and a large number of other functional groups, which can be utilised for binding the dyestuff molecules. Examples of suitable backbone polymers are polyethyleneimines, polylysine, polyamides and low-molecular-weight polycarboxylic acids.

The first example of the patent mentioned describes the synthesis of a polymer dyestuff comprising polyethyleneimine and fluorescein isothiocyanate (FITC), which contains 70 dyestuff molecules per molecule of polyethyleneimine. According to Example 7, determination of the quantum yield of such a polymer dyestuff containing 80 bound fluorescein units gives a value of only 4%. Hence, this polymer at one hundred times the molecular weight has only about three times the fluorescence of monomeric FITC.

German Offenlegungsschrift 3,921,498 describes fluorescent polymer reagents prepared by reaction of copolymers containing dicarboxylic anhydride groups with dyestuffs containing amino groups. According to Example 4, reagents of this type are reported to give high quantum yields of more than 60%.

Despite these high quantum yields, the molar amplifications, compared with the monomer dyestuffs used, are not yet satisfactory, since the molecular weights of the water-soluble polymer backbone are still too low. The degree of amplification of the system is determined by the intensity of the fluorescence, which in turn can be calculated from the product of molar extinction and quantum yield of fluorescence.

Accordingly, in order to achieve high amplification compared with the monomer dyestuff used, both factors (molar extinction and quantum yield of fluorescence) have to be as high as possible.

However, in the previously described polymer systems, at least one of these two factors is too low for achieving the desired high amplification.

Polymer dyestuffs have now been found which are characterised in that they have the general structure of the formula (I)

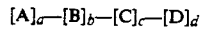

(I)

in which

A denotes a water-solubilising building block,

B denotes a fluorescent dyestuff molecule covalently bound via an ester, acid amide, urethane, urea and/or thiourea grouping, C denotes an aromatic building block or a second fluorescent dyestuff which is covalently bound via an ester, acid-amide, urethane, urea and/or thiourea grouping and is complementary to fluorescent dyestuff B, D denotes a monomer building block which makes a covalent linkage to a protein and, if desired, to components B and/or C possible, and a, b, c and d represent the percentages by weight of components A, B, C and D, which together add up to 100% by weight.

The water-solubilising building blocks A can be ionic or nonionic. They can be, for example, acrylic acid, methacrylic, acid, acrylamide, methacrylamide or derivatives thereof. Examples of suitable derivatives are: 2-acryloylamino-2-methyl-propanesulphonic acid, dialkylamino-alkyl (meth)acrylates and dialkylaminoalkyl-(meth)-acrylamides, such as dimethylaminoethyl methacrylate, dimethylamino-propyl-acrylamide and the quaternised compounds derived from such (meth)acrylates and (meth)acrylamides. Further examples of suitable compounds are: N-vinylpyrrolidone, N-vinylpiperidone, N-vinylcaprolactam, N-vinylformamide, N-vinylacetamide, N-vinyl-N-methyl-acetamide and methyl N-vinyl-O-methylurethane.

A second fluorescent dyestuff (=possible component C) complementary to B is understood to mean a fluorescent dyestuff which, after excitation, emits light in a wavelength range which differs, for example, by ±30 nm from the wavelength at which the particular fluorescent dyestuff B has its maximum absorption.

Examples of suitable fluorescent dyestuffs B and, if present, C are coumarins of the formula (II)

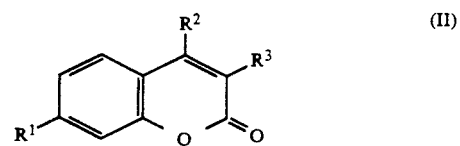

in which $R^1$ represents O-alkyl, N(alkyl)$_2$, NH-alkyl, NH-SO$_2$-alkyl, O-trimethylsilyl or NH-SO$_2$-aryl, $R^2$ represents hydrogen, cyano, chlorine, hydroxyl, alkyl or aryl and $R^3$ represents phenyl or hetaryl.

Alkyl preferably denotes $C_1$- to $C_6$-alkyl, aryl preferably phenyl, alkylene preferably $C_1$-$C_6$-alkylene and hetaryl preferably (benzo)thiazolyl

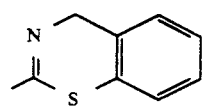

$R^1$ can also denote

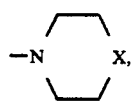

in which X represents oxygen, N—C$_1$- to C$_4$-alkyl or (CH$_2$)$_n$, in which n can be 0 or 1.

Furthermore, coumarins of the formula (III)

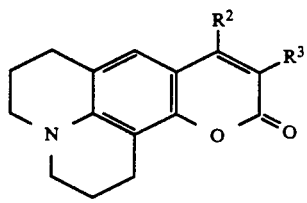

in which R$^2$ and R$^3$ have the meaning given in formula (II), are suitable.

The coumarins of the formulae (II) and (III) preferably contain on one of the substituents R$^1$, R$^2$ and R$^3$ a functional group for linking the dyestuff with a monomer building block D or the polymer available therefrom. NH$_2$ or OH groups are particularly suitable for this purpose.

Carbostyrils of the formula (IV)

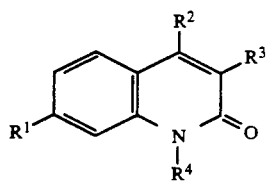

in which
R$^1$, R$^2$ and R$^3$ have the meanings given for the coumarins (see formulae (II) and (III)) and
R$^4$ represents alkyl, preferably C$_1$- to C$_6$-alkyl,
are also suitable.

In this case, too, one of the substituents preferably contains a functional group for linkage with a monomer building block D or the polymer available therefrom.

Furthermore, pyrazolines of the formula (V)

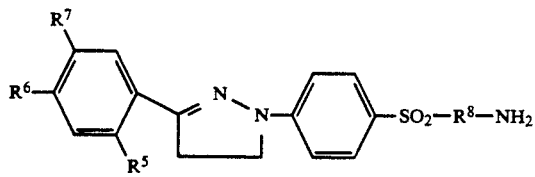

in which
R$^5$ represents hydrogen or methyl,
R$^6$ and R$^7$, independently of one another, represent hydrogen or chlorine and
R$^8$ represents alkylene, $$\begin{array}{c} \text{N—alkylene} \\ | \\ \text{alkyl} \end{array}$$

or alkylene-O-alkylene, in which alkyl and alkylene can, for example, denote C$_1$-to C$_6$-alkyl or C$_1$- to C$_6$-alkylene, are suitable.

Naphthalimides of the formula (VI)

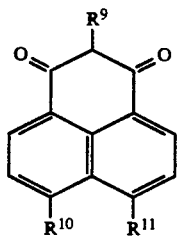

in which
R$^9$ represents alkyl and
R$^{10}$ and R$^{11}$, independently of one another, represent hydrogen, O-alkyl or N(alkyl)$_2$,
in which alkyl in each case preferably denotes C$_1$- to C$_6$-alkyl and one of the radicals R$^9$, R$^{10}$ or R$^{11}$ carries an NH$_2$ group for linkage with a monomer building block D or the polymer available therefrom, are also suitable.

Pyrenes of the formula (VII)

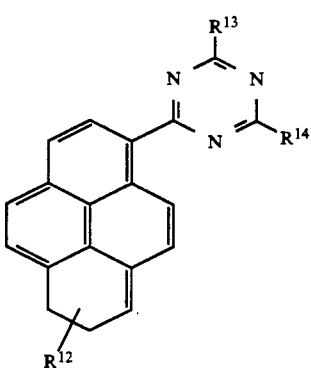

in which
R$^{12}$ represents hydorgen or SO$_3$H and
R$^{13}$ and R$^{14}$, independently of one another, represent O-alkyl or N(alkyl)$_2$,
in which alkyl preferably denotes C$_1$- to C$_6$-alkyl and one of the radicals R$^{13}$ or R$^{14}$ carries an NH$_2$ group for linkage with a monomer building block D or the polymer available therefrom, are also suitable.

Fluoresceins of the formula (VIII)

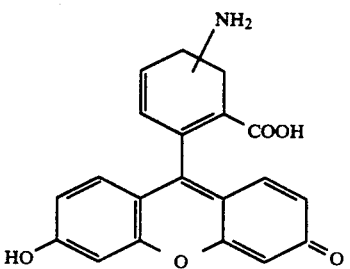

and rhodanines of the formula (IX)

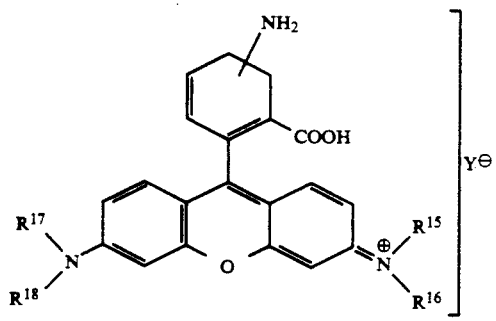

in which
Y⊕ denotes a colourless anion, for example Cl⊖, Br⊖, I⊖, HSO₄⊖,

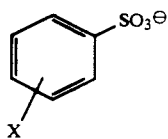

X is Cl, Br, I, CH₃ and
$R^{15}$ to $R^{18}$, independently of one another, represent alkyl or

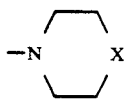

in which alkyl preferably denotes $C_1$- to $C_6$-alkyl and X represents oxygen, N—$C_1$- to $C_4$-alkyl or $(CH_2)_n$, in which n can be zero or 1, are also suitable.

N⊖$R^{15}R^{16}$ and/or $NR^{17}R^{18}$, together with the aromatic ring to which they are bound, can also form a polycyclic system, for example a system of the formula (X) or (XI).

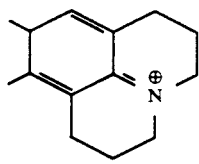

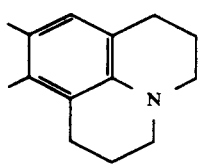

These and other suitable dyestuffs are known (see, for example, "The Chemistry of Synthetic Dyes", Vol. V, Academic Press (1971) and "Fluorescent Whitening Agents", G. Thieme Verlag Stuttgart (1975)).

If C is an aromatic building block, examples thereof are styrene, α-methylstyrene or a compound of the formula (XII)

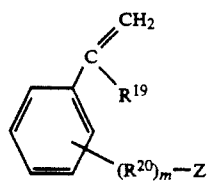

in which
$R^{19}$ denotes hydrogen or methyl,
$R^{20}$ denotes $CH_2$ or $SO_2$,
m denotes zero or 1 and
Z denotes halogen, $SO_2$—$CH_2$—$CH_2$-halogen, OMe, SO—$CH_3$ or methyl.

Halogen preferably represents chlorine, bromine or iodine, in particular chlorine or bromine, and Me an equivalent of a metal, for example sodium.

1- and 2-vinylnaphthalene, 1-vinylcarbazole and compounds which are analogous to those of the formula (XII), but contain naphthalene or carbazole as the aromatic parent structure, and (meth)acrylamides and (meth)acrylates derived from aromatic amines, phenols, aromatic hydroxycarboxylic, hydroxysulphonic, aminocarboxylic and aminosulphonic acids of the formula (XIII)

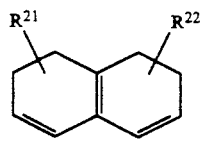

in which
$R^{21}$ represents hydrogen, $SO_3H$, COOH, $SO_3Me$ or COOMe, in which Me denotes an equivalent of a metal, for example sodium, and
$R^{22}$ represents

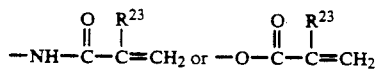

where $R^{23}$ is hydrogen or methyl, are also suitable.

The monomer building blocks D contain reactive or activatable groups which make a covalent bond to a protein and, if desired, to components B and/or C possible. Examples of such groups can be acid halide, imidoester, benzotriazolyl, isocyanate, isothiocyanate, oxirane or diimide groups. The polymerisable portion of D can be, for example, an acrylic, methacrylic, vinyl or styryl radical. D is preferably (meth)acryloyl chloride, N-hydroxy-succinimidyl (meth)acrylate, N-hydroxyphthalimidyl (meth)acrylate, N-(meth)acryloylbenzotriazole, 3- or 4-isothiocyanatophenyl (meth)acrylate, 2-isocyanatoethyl (meth)acrylate, isocyanatoisopropenylbenzene, isopropenyl-α,α-dimethylbenzyl isocyanate, vinyloxirane or a combination of (meth)acrylic acid with carbodiimides.

The protein to which D can be covalently bound can be, for example, an antibody, an antigen, a haptene or a nucleic acid.

a is, for example, between 0 and 90% by weight, b is, for example, between 5 and 50% by weight, c is, for example, between 5 and 89.99% by weight and d is, for example, between 0.01 and 10% by weight. Preferably, a is zero, i.e. separate water-solubilising building blocks are not present. The sum b+c+d then adds up to 100% by weight and b is preferably between 10 and 40% by weight, c is preferably between 59 and 89.95% by weight and d is preferably between 0.05 and 5% by weight.

Of the polymer dyestuffs according to the invention of the formula (I), those are preferred in which C denotes: a compound of the formula (XIII), sodium styrenesulphonate or a fluorescent dyestuff complementary to B within the sense of the abovementioned definition and containing at least one carboxyl or sulpho group and/or at least one carboxylate or sulphonate group, C being bound covalently via an ester, acid amide, urethane, urea and/or thiourea grouping.

A particularly preferred example of a dyestuff B and a dyestuff C complementary thereto is rhodamine B as dyestuff B and fluorescein as dyestuff C.

In particularly preferred polymer dyestuffs according to the invention of the formula (I), B represents a coumarin of the formula (II) bound via an ester, acid amide, urethane, urea and/or thiourea grouping, C represents sodium styrene sulphonate, D represents (meth)acryloyl chloride, N-hydroxy-succinimidyl (meth)acrylate, N-hydroxy-phthalimidyl (meth)acrylate, N-(meth)acryloylbenzotriazole, 3- or 4-isothiocyanatophenyl (meth)acrylate, 2-isocyanatoethyl (meth)acrylate, isocyanatostyrene, isocyanatoisopropenylbenzene, isopropenyl-α,α-dimethylbenzyl isocyanate, vinyloxirane or a combination of (meth)acrylic acid with carbodiimides, a represents zero, b represents 12 to 35% by weight, c represents 62 to 85% by weight and d represents 0.07 to 4.5% by weight.

Polymer dyestuffs according to the invention of the formula (I) can be prepared, for example, by free-radical polymerisation known per se of components A to D. Examples of suitable compounds for forming free radicals are peroxides and azo compounds, such as benzoyl peroxide and azobisisobutyronitrile and examples of suitable solvents are dimethylformamide and dimethyl sulphoxide.

Dyestuff molecules B and C and/or the aromatic building blocks C can be incorporated, for example, by copolymerisation of the corresponding dyestuff or aromatic monomers, for example (meth)acrylic esters or (meth)acrylamides thereof, or by reaction of preferably amino-containing dyestuffs or aromatic building blocks with reactive groups of the polymer backbone in a polymeranalogous reaction.

For D examples of suitable reactive groups and groups which can be rendered reactive are acid halide, imidoester, benzotriazolyl, isocyanato, isothiocyanato, oxirane or diimide groups. If D contains acid halide groups, it is advantageous to use proton scavengers, for example tertiary amines. Suitable solvents for incorporating dyestuffs B and C and/or aromatic building blocks C and for activating the reactive groups incorporated by polymerisation for the purpose of linking them with biological material are those which are inert towards the reactive groups, for example dimethylformamide, dimethyl sulphoxide, dimethylacetamide and acetonitrile.

Activation of reactive groups which are sensitive to hydrolysis for the purpose of linking them with biological materials can be carried out, for example, by means of amino alcohols $H_2N-R^{24}-OH$ (where $R^{24}$ is $C_1$- to $C_{12}$-alkylene) either before or after polymerisation, resulting in OH-functional groups which in turn can be activated, for example, by conversion into a trifluoromethanesulphonyl, methanesulphonyl, trifluoroacetyl, benzenesulphonyl, carboxybenzene-3-sulphonyl or p-toluenesulphonyl group.

Furthermore, it is possible to incorporate for this purpose monomers which already contain an aliphatic alcohol group, such as hydroxyalkyl (meth)acrylates, for example hydroxyethyl (meth)acrylate, hydroxypropyl (meth)acrylate or butanediol mono(meth)acrylate, which can also be activated.

If aqueous reaction media are not necessary for the linkage of the biological material with the polymer dyestuff or the reactive group is stable to hydrolysis, the dyestuff polymers can be reacted directly with the biological material without prior activation.

After activation has been carried out, the polymer dyestuff can be isolated by methods known per se, for example by evaporation of the solvent and/or precipitation of the polymer dyestuff in a suitable organic medium.

Any excess reagents can be separated off either during precipitation of the polymer dyestuff, by repeated reprecipitation or, in the case of water-soluble reagents, also by dialysis or ultrafiltration.

The purified polymer dyestuff can then be dried, thus giving the polymer dyestuffs according to the invention.

The activated dyestuff polymer can then be reacted with the biological substrate (e.g. antibody or suitably functionalised oligonucleotide) in aqueous solution. The mixture obtained can either be used in tests directly or even after previous purification (e.g. immuno assay or gene probe test).

Suitable functionalised oligonucleotides are known. They are understood to mean, for example, oligonucleotides containing amino, mercapto or hydroxyl functions via an internal spacer.

A crucial property for determining the performance of such tests is sensitivity. In most testing procedures customary today it is achieved by using radioactive markers.

However, this method has serious disadvantages in practical application (radiation risk, decomposability of the substances, difficult waste disposal, special laboratory equipment, special personnel training), which have so far prevented extension of this intrinsically advantageous powerful test to routine processes (see, for example, WO 88-02784 and Pharmacia of 21.4.1988).

Several attempts have been made to replace radioactive labelling by a problem-free dyestuff labelling. This circumvents the disadvantage of radioactive labelling, but the sensitivities achieved therewith are not sufficient for many tests (see, for example, Nucleic Acids This is where the polymer dyestuffs according to the invention bring the advantage of increased sensitivity without use of radioactivity.

The polymer dyestuffs according to the invention usually have average molecular weights in the order of $\overline{M}_n = 2 \times 10^3$ to $5 \times 10^6$ dalton. Molecular weights of about $10^4$ to $10^6$ dalton are preferred.

Under conventional conditions of analysis, at least 0.1%, preferably at least 1%, of the polymer dyestuffs is soluble in aqueous media.

Conventional conditions of analysis are those present in biological tests, in particular in binding analysis processes, such as immunoassays or gene probe tests. These conditions comprise, for example, temperatures of up to about 70° C. and pH values of between about 3 and 11. In specific tests, it is possible to depart from these values. The essential feature is the water solubility of the polymer dyestuffs, since this enables the dyestuffs to be used in biological analytical processes.

The polymer dyestuffs according to the invention show much higher intensity of fluorescence than known polymer dyestuffs, since, by using them, in addition to high molar extinctions, high quantum yields can be achieved at the same time. Polymer dyestuffs according to the invention frequently reach degrees of amplification of more than 100. (See Example 6).

EXAMPLE 1

Preparation of polymerisable dyestuff monomers coumarin Ib 1.35 g of acryloyl chloride, dissolved in 4 ml of $CH_2Cl_2$, are added dropwise at 0° C. under an $N_2$ atmosphere to 4 g of coumarin Ia ($R_1$=NEt$_2$, $R_2$=H, $R_3$=

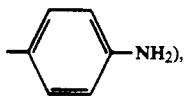

dissolved in 65 ml of $CH_2Cl_2$. The mixture is then warmed to room temperature and additionally stirred for 2 hours, the precipitate formed is filtered off with suction, washed with $CH_2Cl_2$ and dried at room temperature in a high vacuum.

The yield of coumarin Ib is quantitative.

EXAMPLE 2

Preparation of polymerisable dyestuff monomers coumarin IIb 0.9 g of acryloyl chloride, dissolved in 5 ml of DMAC, is added dropwise at 0° C. under an $N_2$ atmosphere to 4 g of coumarin IIa ($R_1$=$C_6H_5$—$SO_2$—NH—, $R_2$=H, $R^3$=

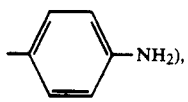

dissolved in 50 ml of DMAC. After dropwise addition of half of the solution, 1.03 g of triethylamine, dissolved in 5 ml of DMAC, is added at the same time. After dropwise addition is complete, the mixture is warmed to room temperature and additionally stirred for 2 hours, the precipitate formed is filtered off, the filtrate is concentrated in a high vacuum and crystallised from ether. Yield of coumarin IIb 85%.

EXAMPLE 3

Preparation of polymerisable comonomer naphthyl acrylate 4 g of β-naphthol are reacted under the conditions described in Example 2 with 2.48 g of acryloyl chloride and 2.77 g of triethylamine. Yield 78%.

EXAMPLE 4

Preparation of polymerisable reactive groups 5 g of isocyanatoethyl methacrylate, dissolved in 5 ml of $CH_2Cl_2$, are added dropwise at 0° C. to 3.77 g of aminohexanol, dissolved in 45 ml of $CH_2Cl_2$. The mixture is then warmed to room temperature and additionally stirred for 1 hour. The $CH_2Cl_2$ is evaporated in a rotary evaporator in a high vacuum, and the crude product is crystallised from ether. Yield quantitative.

EXAMPLE 5

Preparation of polymer dyestuffs 1 g of coumarin IIb from Example 2 and sodium 2-acrylamido-2-methylpropanesulphonate (Na-AMPS) or sodium p-styrenesulphonate) (Na-PSS) or methacrylic acid (MAA), naphthyl acrylate (Ex. 3) and 12 mg of AIBN (total monomer weight 4 g, composition in Table 1) are introduced into 25 ml of DMSO, the apparatus is evacuated, gassed with $N_2$, the process is repeated 3 times, the solution is heated to 65° C. and reacted for 15 hours. The reaction solution is added dropwise to 200 ml of acetone, the precipitate formed is filtered off and dried. The crude polymer is subjected to ultrafiltration (cut-off 10,000 dalton).

Yield 70–80%.

TABLE 1

Comparison of the quantum yields of dyestuff polymers with aliphatic and aromatic comonomers

| | A | B | C | D | E | F |
|---|---|---|---|---|---|---|
| Na-PSS | — | — | 75% | — | 50% | — |
| Na-AMPS | — | 75% | — | 50% | — | — |
| MAA | 75% | — | — | — | — | — |
| Coumarin IIb | 25% | 25% | 25% | 25% | 25% | 100%* |
| Naphthyl acrylate | — | — | — | 25% | 25% | — |
| Quantum yield[1] | 0.23[1] | 0.15[1] | 0.5[1] | 0.25[1] | 0.5[1] 0.39[2] | 0.3[3] 0.41[2] |

*monomer from Ex. 2
[1]in $H_2O$ at pH 9
[2]in DMSO at pH 9
[3]in $H_2O$/pH 9 only partly dissolved

EXAMPLE 6

Dependence on the degree of amplification on the molecular weight of the polymer Polymer $C_2$ was prepared analogously to polymer C from Example 5, except that 12 ml of DMSO were used for polymerisation instead of 20 ml of DMSO.

The molecular weights and their distribution were determined by aqueous gel permeation chromatography, coupled with low-angle laser light scattering (LALLS).

The percentages of the fluorophore in the polymers were determined by the formula $$\frac{\text{Extinction of polymer per gram}}{\text{Extinction of coumarin IIb per gram}} \times 100\%$$

| | Dyestuff % | $M_n$ | $M_w$ | $U = \frac{M_w}{M_n} - 1$ | Degree of amplification |
|---|---|---|---|---|---|
| Polymer C (from Ex. 5) | 22 | 108,000 | 259,000 | 1.39 | 50.8 |
| Polymer $C_2$ | 22 | 337,000 | 787,000 | 1.33 | 158.5 |

EXAMPLE 7

Preparation of a polymer containing two fluorescent dyestuffs which are complementary to each other 2 g of hydroxyethyl methacrylate were dissolved in 8 ml of dimethylacetamide, 20 mg of AIBN were added, the reaction flask was evacuated, gassed with high-purity nitrogen, the process was repeated 3 times, the mixture was heated to 65° C. and allowed to react for 15 hours. After cooling, 10 ml of DMSO and 10 mg of tetramethylrhodamine isothiocyanate were added to the crude solution, and stirring at 80° C. was continued for 6 hours. 250 mg of fluorescein isothiocyanate were then added, and the mixture was stirred at 80° C. for another 15 hours. The product was precipitated from the crude solution in ethyl acetate, filtered off with suction and reprecipitated twice in ethanol/ether and dried in a high vacuum.

The crude polymer was subjected to ultrafiltration as described in Example 5.

The emission spectrum of the polymer, dissolved in water/methanol at a pH of 11, excited at 500 nm, i.e. the extinction maximum of fluorescein, showed a broad shoulder at 575 nm, i.e. the emission wavelength of rhodamine, which contributed 27% of the quantum yield. (Its contribution was calculated from the integral of the total area which corresponded to a total quantum yield of 73%). Accordingly, efficient energy transfer from fluorescein to rhodamine took place, as a result of which the latter became sensitised. The same solution, excited at 549.4 nm, i.e. direct excitation of rhodamine at the extinction maximum, showed an emission whose maximum was 574.7 nm and whose quantum yield was 30%.

EXAMPLE 8

Synthesis of linkable polymer dyestuffs

The procedure was analogous to that of polymer C from Example 5, except that additionally 200 mg of the reactive monomer from Example 4 were added. 1 g of

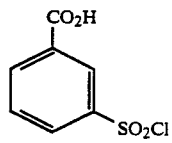

3-(chlorosulphonyl)benzoic acid and, after 30 minutes, 0.5 g of triethylamine were added to the DMSO-containing polymer solution, the mixture was allowed to react at room temperature for 1 hour, and the product was precipitated and subjected to ultrafiltration as described in Example 5.

EXAMPLE 9

100 μg of the aminolink oligonucleotide of sequence CTC GGA TCC CAT CTT CTC CCC TGA GTC TGT (designated SEQ ID NO: 1) (synthesis according to N. D. Sinha and R. M. Cook, Nucleic Acids Research 16, 2659 (1988)) are dissolved in 300 μl of carbonate buffer (pH of 9), and an excess of the polymer fluorescent dyestuff according to Example 8 in 200 μl of carbonate buffer is added. The reaction is carried out at room temperature over a period of 60 hours. Work-up takes place by gel filtration on Biorad-Bio-Gel P 4 or by reversedphase HPLC on RP 18 using triethylammonium acetate/acetonitrile as eluents.

EXAMPLE 10

100 μg of the aminolink oligonucleotide of sequence AT CTA CTG GCT CTT TTT TTT TTT TTT TTT TTT TTT TTT TTT T (designated SEQ ID NO: 2) are dissolved in 200 μl of carbonate buffer (pH of 9), and an excess of the polymer fluorescent dyestuff according to Example 8 in 300 μl of carbonate buffer is added, and the mixture is stirred at room temperature for 60 hours. For work-up, the entire reaction mixture is applied to a poly A-sepharose 4B column (5 ml) (Pharmacia). The non-bound dyestuff is washed off using the application buffer (A) (see below, 20 ml), the column is washed with the elution buffer (B) (see below, 30 ml) and the coupling product is finally washed off using elution buffer (C) (see below, 40 ml).

Application buffer (A): 1.513 g of tris, 10.23 g of NaCl, 0.56 g of EDTA are dissolved in 750 ml of water, and the solution is made up to 1 liter with formamide.

Elution buffer (B): 7.45 g of KCl are dissolved in 100 ml of application buffer A.

Elution buffer (C): 3.7 g of KCl and 50 ml of formamide are made up to 100 ml with application buffer A.

By using the aminolink oligonucleotides thus labelled in DNA probe tests, increased sensitivity compared with DNA probes labelled with monomer fluorescent dyestuffs is achieved.

EXAMPLE 11

Use of polymer fluorescent dyestuffs in immunological test systems 10 mg of the polymer dyestuff according to Example 8 are dissolved in 10 ml of 0.5 molar carbonate/bicarbonate buffer at a pH of 9.0. 5 mg of phosphodiesterase (from rattlesnake venom from Sigma) in 5 ml of carbonate buffer of pH 9.0 (0.5M) are added, the mixture is stirred at room temperature for 4 hours and then allowed to continue the reaction overnight in a refrigerator. The pH is then brought to 11 with 1N NaOH, and the crude solution is chromatographed (sephacryl S-500 from Pharmacia in 0.02M carbonate buffer of pH 11, diameter of the column 16 mm, height 100 cm).

After 500 ml of the carbonate buffer had passed the column was washed with 1000 ml of a 2.5% strength ammonia solution in water.

The first peak at an elution volume of 200 ml contains PDE activity* and flourescence.

*Testing for PDE-activity: 400 μl of eluate 600 μl of 0.1M tris buffer of pH 8.8 200 μl of 0.3M magnesium acetate and 1000 μl of mmolar bis(p-nitrophenyl) phosphate are reacted at 37° C. for 105 minutes, leading to a yellow colour.

Unconverted dyestuff and unconverted PDE are eluted later.

---

What is claimed is:

1. A polymer dyestuff of the formula (I):

$$[A]_a-[B]_b-[C]_c-[D]_d \quad (I)$$

in which
A denotes a water-solubilizing building block;
B denotes a fluorescent dyestuff molecule covalently bound via an ester, acid amide, urethane, urea and/or thiourea grouping;
C denotes an aromatic building block or a second fluorescent dyestuff which is covalently bound via an ester, acid amide, urethane, urea and/or thiourea grouping and is complementary to fluorescent dyestuff B;
D denotes a monomer building block which makes a covalent linkage to a protein and, optionally, to components B and/or C possible; and
a,b,c and d represent the percentages by weight of components A, B, C and D, wherein:
a is between 0 and 90% by weight;
b is between 5 and 50% by weight;
c is between 5 and 89.99% by weight; and
d is between 0.01 and 10% by weight;
the sum of a+b+c+d being 100% by weight.

2. A polymer dyestuff of claim 1, in which component C is a fluorescent dyestuff which, after excitation, emits light in a wavelength range which differs by ±20 nm from the wavelength at which the particular fluorescent dyestuff B has its maximum absorption.

3. A polymer dyestuff of claim 1, in which component A is an acrylic acid, a methacrylic acid, an acrylamide, a methacrylamide or derivatives thereof.

4. A polymer dyestuff of claim 1, in which component C is styrene, α-methylstyrene, a compound of the formula (XII):

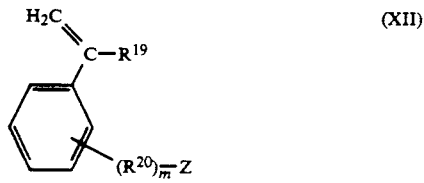

in which
$R^{19}$ denotes hydrogen or methyl,
$R^{20}$ denotes $CH_2$ or $SO_2$,
m denotes zero or 1 and
Z denotes halogen, $SO_2-CH_2-CH_2$-halogen, OMe, SO-$CH_3$ or methyl whereby Me denotes an equivalent of a metal,
1-vinylnaphthalene, 2-vinylnaphthalene, 1-vinylcarbazole, a compound of the formula (XIIa) or (XIIb):

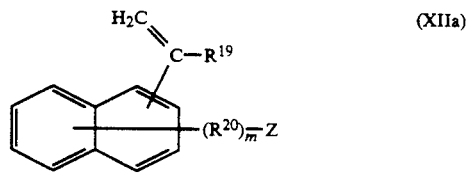

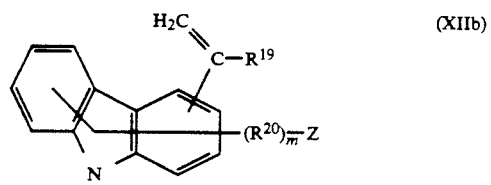

in which
$R^{19}$, $R^{20}$, m and Z have the meaning indicated above;
or a (meth)acrylamide or (meth)acrylate derivative which is derived from (meth)acrylchloride and an aromatic amine, phenol, aromatic hydroxycarboxylic, hydroxysulphonic, aminocarboxlic and aminosulphonic acid of the formula (XIII):

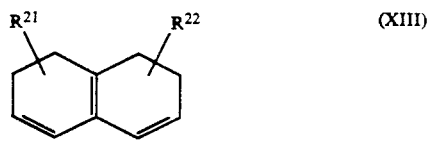

in which
$R^{21}$ represents hydrogen, $SO_3H$, COOH, $SO_3Me$ or COOMe, in which Me denotes an equivalent of a metal, and
$R^{22}$ represents

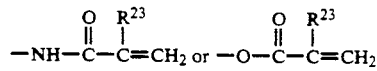

where $R^{23}$ is hydrogen or methyl

5. A polymer dyestuff of claim 1, in which component D is a (meth)acryloyl chloride, N-hydroxy-succinimidyl(meth)acrylate, N-hydroxy-phthalimidyl(meth)acrylate, N-(meth)acryloylbenzotriazole, 3- or 4-isothiocyanatophenyl(meth)acrylate, 2-isocyanatoethyl(meth)acrylate, isocyanatoisopropenylbenzene, isopropenyl-$\alpha,\alpha$-dimethylbenzyl isocyanate, vinyloxirane or a combination of (meth)acrylic acid with a carbodiimide.

6. A polymer dyestuff of claim 1, in which component B is rhodamine B and component C is fluorescein.

* * * * *